(12) United States Patent
Emch et al.

(10) Patent No.: US 6,422,072 B1
(45) Date of Patent: Jul. 23, 2002

(54) DEVICE FOR MEASURING PROPERTIES OF A LONGITUDINALLY MOVED SPECIMEN SUCH AS YARN

(75) Inventors: Beat Emch, Eglisau; Rolf Joss, Horgen; Felix Brunner, Wetzikon; Bernhard Hitlebrand, Uster; Peter Schilling, Siebnen; Beat Keller, Dübendorf; Hanspeter Wepfer, Unterstammheim, all of (CH)

(73) Assignee: Zellweger Luwa AG, Uster (CH)

( * ) Notice: Subject to any disclaimer, the term of this patent is extended or adjusted under 35 U.S.C. 154(b) by 0 days.

(21) Appl. No.: 09/274,329

(22) Filed: Mar. 23, 1999

(30) Foreign Application Priority Data

Mar. 25, 1998 (CH) .............................................. 0698/98

(51) Int. Cl.⁷ .............................................. G01L 5/04
(52) U.S. Cl. ...................................................... 73/160
(58) Field of Search ...................... 73/160, 159, 104, 73/861.04, 800; 324/558; 242/481.7, 477.6

(56) References Cited

U.S. PATENT DOCUMENTS

| | | | | |
|---|---|---|---|---|
| 3,260,106 A | * | 7/1966 | Hull et al. ...................... 73/144 |
| 4,058,962 A | * | 11/1977 | Spescha et al. ................ 73/160 |
| 4,152,931 A | * | 5/1979 | Mannhart ...................... 73/160 |
| 4,168,604 A | * | 9/1979 | Mannhart ...................... 73/160 |
| 4,774,673 A | | 9/1988 | Aemmer ....................... 700/144 |
| 4,993,650 A | * | 2/1991 | Nickell ....................... 242/18 R |
| 5,124,928 A | | 6/1992 | Aemmer ....................... 700/144 |
| 5,592,849 A | * | 1/1997 | Nakade et al. ................. 73/160 |
| 5,636,803 A | * | 6/1997 | Aschmann et al. ........... 242/36 |
| 5,768,938 A | | 6/1998 | Schilling et al. .............. 73/160 |
| 6,065,333 A | * | 5/2000 | Aschmann et al. ........... 73/160 |

FOREIGN PATENT DOCUMENTS

| | | |
|---|---|---|
| DE | 36 35 267 | 5/1987 |
| EP | 0 679 862 | 11/1995 |
| EP | 0 570 836 | 1/1997 |
| EP | 0 821 089 | 1/1998 |
| WO | 97/36032 | 10/1997 |

* cited by examiner

Primary Examiner—Benjamin R. Fuller
Assistant Examiner—Octavia Davis
(74) Attorney, Agent, or Firm—Burns, Doane, Swecker & Mathis, L.L.P.

(57) ABSTRACT

The invention relates to a device for measuring properties of a longitudinally moved test material in a measuring cell. In order to provide a device which is easier to adapt to the requirements of a customer and to the special conditions of a production machine for longitudinally moved test material, the measuring cell (1) is connected to a processor (6), which is associated exclusively with the measuring cell.

5 Claims, 2 Drawing Sheets

DEVICE FOR MEASURING PROPERTIES OF A LONGITUDINALLY MOVED SPECIMEN SUCH AS YARN

Figure 1:
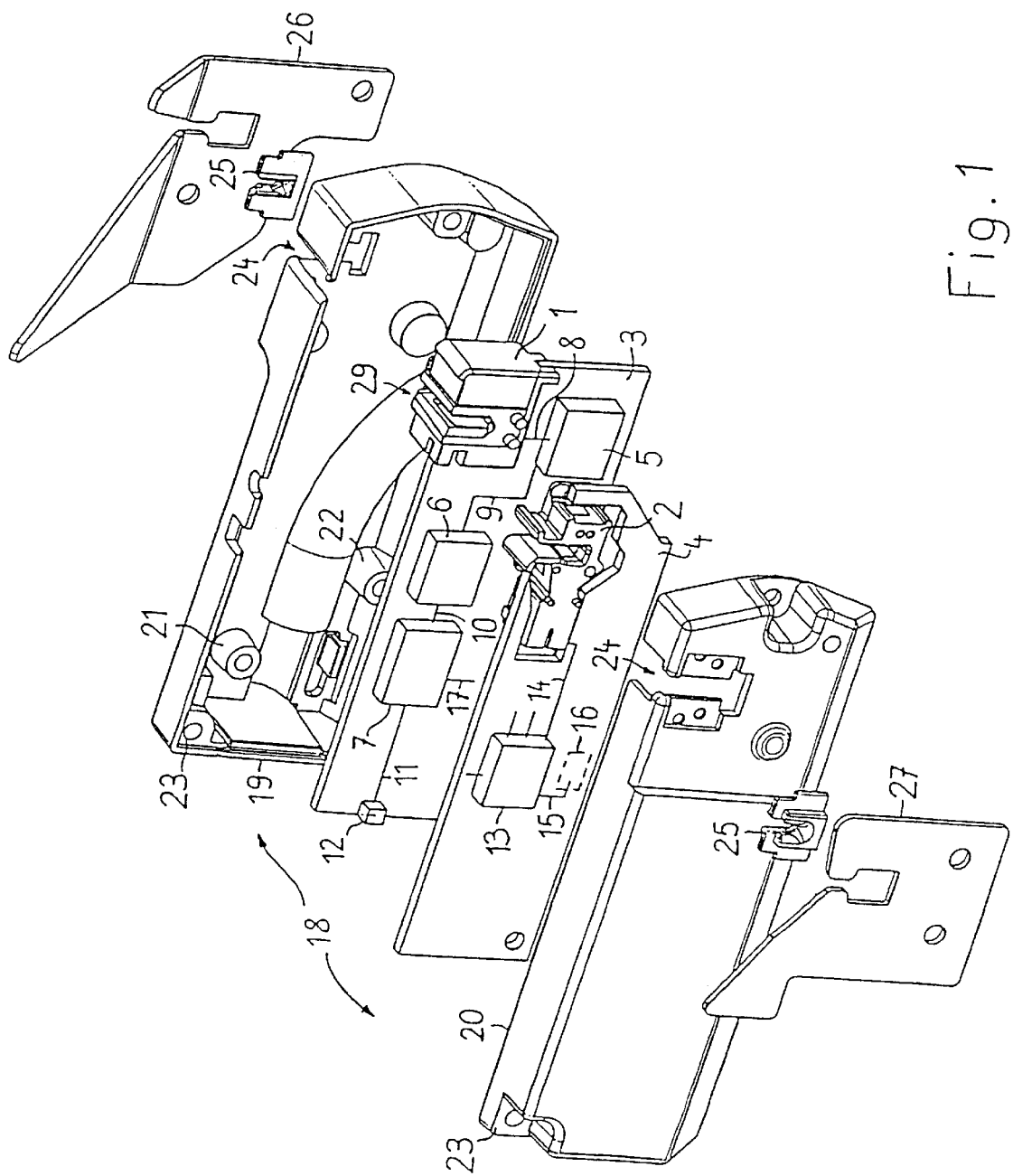

The invention relates to a device for measuring properties of a longitudinally moved test material in a measuring cell. More particularly, the invention is concerned with means for measuring properties of yarns while such yarns are being manufactured.

In conventional yarn manufacturing practice, spinning frames and spooling frames are used to simultaneously process many yarns. Each yarn is processed while the yarn is moving in its lengthwise direction along a path at its own work station or yarn position. The several yarn positions are disposed in a row extending generally transverse to the several yarn paths.

The presently used equipment intended for measuring properties of yarn and disposed on a spinning or spooling frame, comprises three parts connected by lines, namely the measuring head with the measuring cell, the evaluation unit and the control unit. One or more evaluation units are connected to a control unit and one or more measuring heads are connected to each evaluation unit. The measuring heads supply unprocessed, analog or alternatively analog and digital signals to the evaluation unit. The evaluation unit however also supplies signals to the measuring head. The evaluation unit evaluates the signals, e.g. by comparing them with threshold values, and supplies processed and possibly also digitized signals to the control unit. Usually, one control unit per spinning frame or per spooling frame is the norm.

Such known devices take up a great deal of room. In order to take up as little room as possible in the spinning or spooling frame of the yarn, the measuring head is designed as simply as possible. It may therefore perform only a single function, namely measuring. Other functions are therefore performed in the evaluation unit. This means that such a known device comprises numerous parts, which are connected to one another by numerous lines and connectors, and its initial cost is correspondingly high. The mounting onto the spinning and spooling frame is accordingly also costly and complex. Since each measuring head is also of a specific design geared to the frame onto which it is to be mounted, this also means that, for each type of spinning or spooling frame, a special measuring head and a separate evaluation unit are manufactured.

An object of the present invention is to provide a device which is easier to adapt to the requirements of a customer and to the special conditions of a production machine for longitudinally moved test material. This object is achieved by a device, in which a measuring cell for the longitudinally moved test material is connected directly to an associated processor provided exclusively for said measuring cell. The measuring cell and the processor are permanently connected to one another and disposed on a first carrier or combined in a separate housing. In this case, there is only one output for a line for transmitting digitized signals, which have already undergone a first evaluation. Such a device may comprise a plurality of measuring cells for various tasks, which together are in turn disposed on a further carrier or in a further housing. By various tasks are meant, for example, various types of measurement, e.g., optical or capacitive measurements of the cross section or of the mass of the test material, impurity measurements, measurements of the hairiness of a yarn etc. The processor preferably takes the form of a so-called ASIC module, i.e., an application specific integrated component. It is always of an identical construction and may perform the same functions irrespective of whether it is connected to a measuring cell for optical measurement, a measuring cell for capacitive measurement etc. In particular, it is used to amplify and convert signals. For said reason, the ASIC module comprises at least one analog-to-digital converter. It therefore often has a plurality of inputs for analog signals and one output for digital signals. The further carrier comprises, besides the first carrier or carriers or housings with the measuring cells, a processor, in particular a digital signal processor (DSP), which has a plurality of inputs for connections to a plurality of ASIC modules. The first carriers with the measuring cells are connected by detachable connections, e.g., plug connectors, to the further carrier.

The advantages achieved by the device according to the invention are in particular that it is possible to dispense with a separate evaluation unit provided some distance away from the measuring head. There are therefore far fewer connections between measuring heads, evaluation units and control units of a spinning or spooling frame and so, because numerous connectors and printed-circuit boards are also dispensed with, operational reliability is increased. Since the device now comprises a low number of standardized parts, the manufacture and holding in storage of said parts by the manufacturer is likewise simplified. As larger piece numbers of each part are achieved, a greater accuracy and effort may go into the testing of said parts because specific test equipment for said purpose is worthwhile. Since the "intelligence" has been relocated in the measuring heads and decentralized, it is also only necessary to provide one cable from the measuring head to the production point and said cable carries digital signals, thereby making the system more fail-safe. The software is already stored in the measuring head and no longer has to be loaded there on demand.

Figure 2:
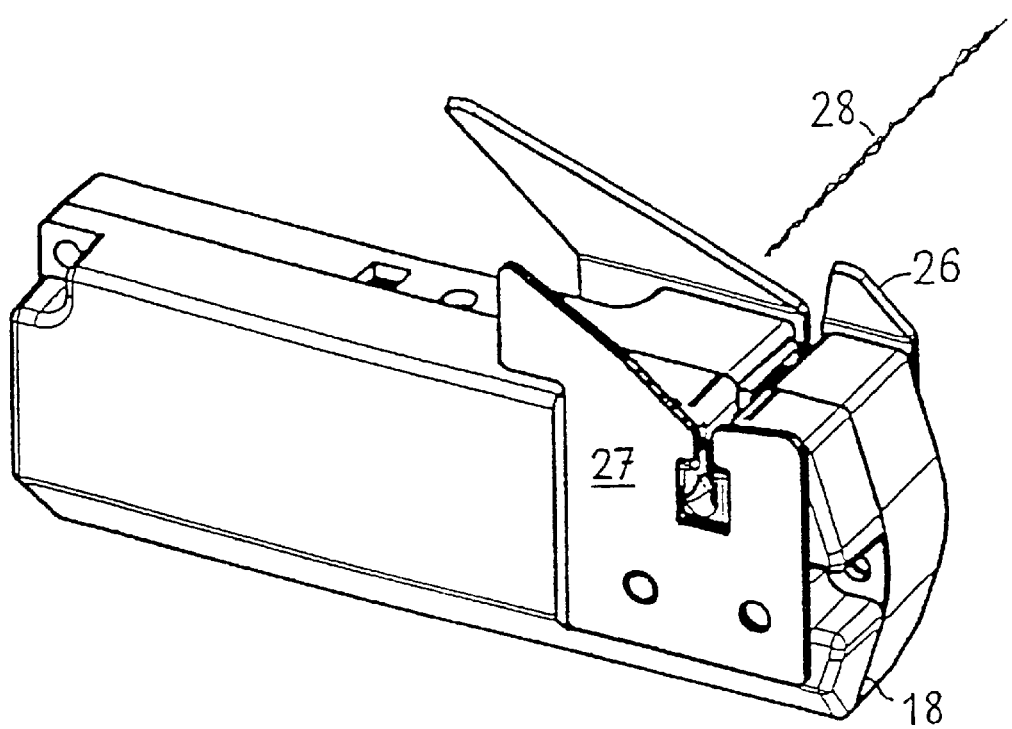

There follows a detailed description of the invention by way of an example and with reference to the accompanying drawings. In the drawings:

FIG. 1 is a view of the device according to the invention, showing the individual parts in an exploded manner, and FIG. 2 is a perspective external view of the device.

FIG. 1 shows a device for measuring properties of a longitudinally moved test material with a first measuring cell 1 and a second measuring cell 2. The first measuring cell 1 may be, for example, an optical or capacitive sensor of the type which is already used in known slub catchers and measures the cross section or the mass of the test material. The second measuring cell 2 may, for example, take the form of a sensor which detects impurities in the test material or which measures other properties of the test material such as, for example, hairiness, color, twist etc. In said case, the measuring cell 1 and the measuring cell 2 are fastened in each case on a first carrier 3 and 4 respectively. The first carrier 3, 4 takes the form of, for example, a printed-circuit board. On the first carrier 3 further components are fastened, namely in each case a processor 5 and 6 as well as a computer 7. The processor 5 takes the form of a so-called ASIC and amplifies the output signals of the measuring cell 1. Said processors 5 is tuned to the measuring cell 1 and processes analog signals. The processor 6 likewise takes the form of an ASIC (application specific integrated circuit) but is designed for mixed signals. In other words, it may process analog and digital signals. The computer 7 takes the form of a digital signal processor (so-called DSP). Thus, the computer 7 is permanently connected by the two processors 5 and 6 and by lines 8, 9, 10 to the measuring cell 1 because all of said elements and also further elements are permanently mounted using the conventional methods onto the first carrier 3 in the form of a printed-circuit board. The computer 7 is further connected by a line 11 to a connector 12. The lines 8 and 9 transmit analog signals while the lines 10 and 11, which form outputs for the processor 6 and the computer 7, transmit digital signals.

The first carrier 4 with the measuring cell 2 likewise comprises a processor 13, which is connected by a line 14 to the measuring cell 2. The processor 13 is identical in construction to the processor 6. In particular, identical components are used for the processors 6 and 13. Said first carrier 4 also preferably takes the form of a printed-circuit board. The processor 13 additionally has a further output 15 leading to a connector 16, which is provided between the two first carriers 3 and 4 and to which a line 17 disposed on the first carrier 3 and connected to the computer 7 leads.

Besides the two first carriers 3 and 4 illustrated here, a further carrier 18 is provided, which in the present case comprises two parts 19, 20 and forms a housing for the two first carriers 3, 4 with the measuring cells 1, 2. The two first carriers 3, 4 are fixed by means of screw-type connections to the two parts 19, 20. Here, it is therefore possible to see parts of the screw-type connections 21, 22. The two parts 19, 20 are fastened to one another likewise by screw-type connections 22, 23. The further carrier 18 is in turn fastened by connections e.g., to a spinning or spooling frame. The further carrier in particular also has an opening 24 for the test material, into which a guide element 25 (schematically shown here as removed from the opening 24) may be inserted. Further guide elements 26, 27 for facilitating insertion of the test material into the opening 24 are provided and fastened likewise to the further carrier 18.

FIG. 2 here shows the assembled device with the guide elements 26, 27, the opening 24 for a test material 28 and the further part 18.

The mode of operation of the device according to the invention is as follows: When, at the assembled device, a test material is introduced into the opening 29 in the measuring cell 1 and moved therein in a known manner in its longitudinal direction, analog signals are produced in the measuring cell 1 and pass via the line 8 into the processor 5.

There, they are processed and supplied via the line 9 to the processor 6, which converts said signals into digital signals. The processing may for example be such that the processor 5 supplies to the measuring cell a carrier signal which is modulated by the test material, the modulated signal being demodulated and amplified in the processor 5. In the processor 6, the signals of the test material are digitized and filtered. During said process the processor 6 may however also supply control signals to the processor 5, e.g., to compensate or cancel out the effect of fouling of the opening. The digitized signals are output through the line 10 to the computer 7, which compares said signals e.g., with threshold values and executes processing steps such as, for example, the application of error algorithms and further evaluations. Via the line 11 and the output or the connector 12 the processed and evaluated signals pass, for example, into the central control system of the machine, on which said device is fastened. It is possible alternatively to omit the processor 5 and connect the measuring cell 1 directly to the processor 6. However, this depends upon the type of measuring cell 1 used and upon the signals which it supplies. If the measuring cell 1 operates according to an optical principle, the above alternative is applicable. If it operates according to a capacitive measuring principle, the processor 5 is highly desirable.

Also provided, in addition to the measuring cell 1, is the measuring cell 2 which likewise measures or scans the test material. Said measuring cell supplies its signal via the line 14 to the processor 13, which amplifies the signal and converts it into a digital signal. The signal may then pass via the output 15, the connector 16 and the line 17 into the computer 7, where it is likewise processed and evaluated. Here, the computer 7 also has the possibility of jointly evaluating the signals from both measuring cells 1 and 2 and outputting values, which are calculated from both signals through combination, via the line 11.

The measuring cells are connected on the respective first carrier permanently to the processor and together form a module. A housing or a further carrier may accommodate a plurality of first carriers or modules. All of said modules supply their already digitized signal to the single computer 7, which is provided on the main module, in the present case the first carrier 3. However, it would also be conceivable to provide a computer on a plurality of modules or even on each module. The preferred result for the entire device or the measuring head is however a single output 12 for evaluated signals which may be supplied to a machine control system. The used processors 5, 6, 13 are all of an identical construction and may all perform the same functions. However, not all functions are always utilized. For example, the processors 5 and 6 perform various processing operations, which in turn do not correspond exactly to the processing operation in the processor 13. Thus, the processors 5, 6 and 13 have a plurality of inputs 30 for analog signals, which are assigned each according to the intended processing operation, but only one output 10, 15 for digital signals. Thus, an identical module 5, 6, 13 designed for many functions is associated with, and permanently connected to, each measuring cell.

What is claims is:

1. Apparatus for attachment to a yarn spinning or spooling frame adjacent to a path of a longitudinally moving yarn being processed therein for measuring and evaluating a plurality of properties of such yarn, said apparatus comprising:

a support unit for attachment to said frame;
   a first generally planar carrier fixed to said support unit and having fastened thereto:
   a first sensor selected from the group consisting of capacitive and optical sensors for measuring a property of said moving yarn,
   first processor means exclusively providing digital output signals derived from the values of the property of the longitudinally moving yarn sensed by said first sensor,
   a computer in the form of a digital signal processor for evaluating said digital output signals from said first processor means and producing digital evaluation signals, and
   an output connector through which the evaluation signals pass for delivery to a control unit of the spinning or spooling frame;
   a second generally planar carrier fixed to said support unit and having fastened thereto:
   a second sensor selected from the group consisting of optical and capacitive sensors for detecting a second property of said longitudinally moving yarn, and
   second processor means exclusively for providing digital output signals derived from the values of said second property of the longitudinally moving yarn sensed by said second sensor; and
   means for connecting said digital output signals from said second processor on said second carrier means to said computer on said first carrier for evaluation by said computer and delivery to a control unit of the spinning or spooling frame through said output connector on said first carrier.

2. Apparatus according to claim 1, wherein said first and second processor means each comprise an ASIC processor module, said ASIC processor modules being of the same construction.

3. Apparatus according to claim 1, wherein each of said carriers comprises a printed circuit board.

4. Apparatus for attachment to a yarn spinning or spooling frame adjacent to a path of a longitudinally moving yarn being processed therein for measuring and evaluating properties of such yarn, said apparatus comprising:

a support unit for attachment to said frame;

a first carrier on said support unit having thereon:
   a first measuring cell for measuring a first property of said longitudinally moving yarn and producing first output measurement signals, and
   first processor means for receiving said first measurement signals and producing digitized output signals;

a second carrier on said support unit and having thereon:
   a second measuring cell for measuring a second property of said longitudinally moving yarn and producing second output measurement signals, and
   second processor means for receiving said second measurement signals and producing digitized output signals; and one of said first and second carriers additionally having thereon:
   a computer connected to said first and second processor means for evaluating the digitized output signals from said first and second processor means, and producing digital evaluation signals, and
   an output connector through which the evaluation signals pass for delivery to a control unit of the spinning or spooling frame.

5. Apparatus according to claim 4, wherein said cells are aligned along a yarn path, and wherein one of said cells makes an optical measurement and another of said cells makes a capacitive measurement.

* * * * *